(12) United States Patent
Bonnefin et al.

(10) Patent No.: US 10,751,442 B2
(45) Date of Patent: Aug. 25, 2020

(54) DRESSING

(75) Inventors: Wayne Bonnefin, Clwyd (GB); Lucy Ballamy, Clwyd (GB)

(73) Assignee: CONVATEC TECHNOLOGIES INC., Las Vegas, NV (US)

(*) Notice: Subject to any disclaimer, the term of this patent is extended or adjusted under 35 U.S.C. 154(b) by 259 days.

(21) Appl. No.: 14/347,974

(22) PCT Filed: Aug. 2, 2012

(86) PCT No.: PCT/GB2012/051883
§ 371 (c)(1),
(2), (4) Date: Apr. 28, 2014

(87) PCT Pub. No.: WO2013/017890
PCT Pub. Date: Feb. 7, 2013

(65) Prior Publication Data
US 2014/0228794 A1    Aug. 14, 2014

(30) Foreign Application Priority Data
Aug. 4, 2011    (GB) .................................. 1113515.9

(51) Int. Cl.
*A61F 13/00* (2006.01)
*A61L 15/42* (2006.01)
*A61L 15/28* (2006.01)

(52) U.S. Cl.
CPC .............. *A61L 15/28* (2013.01); *A61F 13/00* (2013.01); *A61L 15/42* (2013.01)

(58) Field of Classification Search
CPC ................ A61F 13/00; A61F 13/00008; A61F 13/00012; A61L 15/28; A61L 15/42; C08B 11/12

USPC .......................................................... 604/376
See application file for complete search history.

(56) References Cited

U.S. PATENT DOCUMENTS

| 6,075,177 A * | 6/2000 | Bahia et al. .................... 602/43 |
| 2003/0236511 A1 * | 12/2003 | Jones et al. .................. 604/374 |
| 2004/0181182 A1 * | 9/2004 | Shaw ...................... A61L 15/28  602/41 |
| 2005/0182347 A1 * | 8/2005 | Bishop .................. A61F 13/022  602/43 |

FOREIGN PATENT DOCUMENTS

| WO | WO 93/12275 | 6/1993 |
| WO | WO 94/16746 | 8/1994 |

(Continued)

OTHER PUBLICATIONS

PCT/GB2012/051883 International Preliminary Report on Patentability dated Feb. 4, 2014.

(Continued)

*Primary Examiner* — Peter S Vasat
(74) *Attorney, Agent, or Firm* — Taft Stettinius & Hollister LLP; Ryan O. White

(57) ABSTRACT

The invention relates to a chemically modified cellulose based dressing particularly for use in the dressing of wounds but also for use as a packing material. Dressings according to the invention seek to mitigate the problems associated with shrinkage encountered with fibrous dressings made of gel-forming fibres and comprise a compressed body of chemically modified polysaccharide having a density of at least 0.08 $g/cm^3$.

20 Claims, 3 Drawing Sheets

(56) References Cited

FOREIGN PATENT DOCUMENTS

WO     WO 2000/001425     1/2000
WO     WO 2013/017890 A1     2/2013

OTHER PUBLICATIONS

PCT/GB2012/051883 Written Opinion dated Oct. 25, 2012.
PCT/GB2012/051883 International Search Report dated Oct. 25, 2012.

* cited by examiner

| Figure 3 Test | Unit | Average HF-2010/198 Unconverted | Average HF-2010/229 Converted | Average HF-2010/162 Unconverted | Average HF-2010/230 Converted | AQUACEL |
|---|---|---|---|---|---|---|
| GSM | gm$^{-2}$ | 391 | 456 | 501 | 599 | 119 |
| Absorption free swell | g/g | 16.2 | 22.3 | 12.8 | 20.8 | 15.1 |
| Absorption free swell | g/cm$^2$ | 0.63 | 1.02 | 0.64 | 1.24 | 0.18 |
| Retention free swell | g/g | 11.3 | 13.2 | 8.1 | 11.0 | 13.4 |
| Retention free swell | g/cm$^2$ | 0.44 | 0.60 | 0.41 | 0.66 | 0.16 |
| Retention free swell | % | 70 | 59 | 64 | 53 | 91* |
| Lateral Wicking | mm | 90 | 45 | 90 | 52 | 10* |
| Tensile Strength Dry | N/cm | 30.4 | 25.9 | 65 | 53 | 7.8 (MD) 15.8 (TD) |
| Tensile Strength Wet | N/cm | 25.5 | 0.9 | 39.8 | 1.8 | 0.2 (MD) 0.7 (TD) |
| Shrinkage Initial MD | % | 1.0 | -6.6 | -5.3 | -10.3 | 20.5 |
| Shrinkage Initial TD | % | -8.1 | -15.7 | -9.3 | -16.3 | 22.0 |
| Shrinkage Final MD | % | 6.9 | 12.9 | 0.0 | 1.7 | 36.3 |
| Shrinkage Final TD | % | -1.8 | 9.3 | -1.0 | 4.7 | 55.7 |
| Thickness dry | mm | 1.52 | 3.25 | 1.18 | 3.17 | 1.54 |
| Thickness Hydrated | mm | 5.88 | 8.48 | 5.57 | 10.45 | 2.84 |
| Ratio thickness pre: post hydration | n/a | 4.00 | 2.67 | 4.74 | 3.32 | 1.85 |
| Density | gcm$^{-3}$ | 0.2572 | 0.1403 | 0.4237 | 0.1889 | 0.0773 |

Note: MD = machine direction and TD = transverse direction.

DRESSING

The present invention relates to a chemically modified cellulose based dressing particularly for use in the dressing of wounds but also for use as a packing material in the field of dentistry or surgery and to methods for the manufacture of such dressings.

It is known to use carboxymethylated cellulosic materials in situations where a high degree of exudate absorption is required. For example, WO 93/12275 describes the production of various absorbent products capable of absorbing many times their own weight of water. Carboxymethylated fibres form a gel on contact with water or isotonic solutions. WO 94/16746 and WO 00/01425 describe the use of carboxymethylated Lyocell materials in wound dressings where the advantages of gel formation in preventing adherence and therefore reducing wound damage and pain on removal are discussed. GB1397154 concerns heat treating water-soluble carboxyalkyl ether cellulose with a high degree of substitution to modifiy it so that it becomes water insoluble and, when used in a compressed state, is able to absorb and retain fluid.

Known wound dressings comprising gel forming fibres are essentially flat, rectangular and fairly small, typically 20 cm×15 cm. Dressings comprising gel forming fibres have the advantage of high absorbency (typically more than 15 g/g of water), good fluid retention under pressure and good contact with the wound. The transformation of the fibres into a gel on absorption of exudate reduces the tendency of the dressing to adhere to the wound and assists in removal. A disadvantage of such gelling fibre dressings is that although they swell on absorption of exudate which aids wound contact, they are prone to shrinkage in the plane of the dressing which limits their usefulness in certain indications. For example, on highly contoured body parts, shrinkage can cause pulling of the wound. This is particularly so on toes or ears. In addition, in order to counter the risks of lateral shrinkage on less contoured body parts, the care provider is inclined to over compensate for shrinkage by the use of overly large dressings or by overlapping multiple dressings to cover the wound. This makes treatment more costly than necessary.

In certain wounds, which may progress to give less exudate over time, after the formation of a gel, the dressing may begin to dehydrate which can cause further shrinkage.

It would be desirable to bring the benefits of dressings comprising gel forming fibres to wounds without the disadvantages. For instance, by having the dressings available in a form where the problems of shrinkage are ameliorated but where intimate contact between the dressing and the wound is maintained.

It is known to treat wounds with foam dressings which absorb exudate into the porosity of the foam. Although foams can have adequate absorbency for a range of wounds and indications, their ability to retain exudate under pressure makes them unsuitable for some wounds. For example when using a standard foam dressing under compression, a pressure of 40 mmHg may be applied. Due to the poor ability of the foam to retain fluid, wound exudate may be forced out of the foam to the surrounding peri-wound skin which can cause maceration and the spread of bacteria. In addition foams do not make an intimate contact with the wound bed.

The present invention therefore seeks to provide an improved modified cellulose for use in dressings which mitigates the problems associated with shrinkage encountered with fibrous dressings made of gel-forming fibres and mitigates the problems of poor retention encountered with foam dressings.

We have now found that it is possible to give gel-forming properties to a compressed material. Surprisingly the material has reduced contraction on absorption of exudate compared with dressings made from fibrous mats of gel-forming fibres made by needling or hydroentangling.

Accordingly a first aspect of the invention provides a wound dressing comprising a compressed body of chemically modified polysaccharide having a density of at least 0.08 g/cm$^3$.

The compressed body of chemically modified polysaccharide is preferably a cellulose and appears to have the form a close packed structure similar to that seen in the dissolving and ripening stages of the regeneration of cellulose. The compressed body preferably has a density of between 0.080 to 0.50 gcm$^{-3}$, preferably 0.1 gcm$^{-3}$ to 0.45 gcm$^{-3}$ and more preferably 0.1 gcm$^{-3}$ to 0.2 gcm$^{-3}$.

The compressed body appears to have an informal layered structure where the informal layers of the compressed body are weakly associated. The association between the layers of the body is broken by absorption of exudate which causes the layers to expand and spread apart.

An advantage of the expansion of the structure is that the swollen dressing forms an intimate contact with the wound but has been found to have a lower lateral shrinkage compared to that experienced with fibrous mats of gel-forming fibres. The expansion of the dressing on absorption of exudate combined with the gelling action of the fibres may force the dressing into intimate contact with the wound.

A second aspect of the invention provides a dressing comprising a compressed body of cellulose which has been chemically modified to increase its absorbency and which expands on absorption of exudate.

By absorbency we mean absorbency assessed by the method described in British Pharmacopoeia 1993, Addendum 1995, page 1706 for alginate dressings but with substitution of alginate with the dressing under test, which method yields absorbency in terms of weight per unit area and then converted to absorbency in terms of weight ratio (g/g).

The chemical modification may be carboxymethylation of cellulose, cotton or a combination of the two and may be performed by contacting the body with a strong alkali, for example sodium hydroxide and a carboxymethylating agent such as chloracetic acid or a salt thereof such as the sodium salt. These reagents may be applied to the body separately or together. The reaction is conveniently performed in an aqueous system which preferably comprises a water-miscible organic solvent such as ethanol or industrial methylated spirits in order to suppress swelling and dissolution of the carboxymethylated cellulose.

A preferred method of conducting the modification is described in WO 00/01425. In a suitable method, the cellulosic body is loaded into a reaction vessel. Reaction fluid is pumped through the cellulosic material at 65° C. for 90 minutes. The reaction fluid is a solution of an alkali (typically sodium hydroxide) and sodium monochloroacetate in industrial denatured alcohol. After the reaction time, the reaction is neutralised with acid and washed before being dried in a laboratory oven for 1 hour at 40° C.

The compressed, body of the present invention is preferably an absorbent cellulose material manufactured such as that sold as an absorbent by Kettenbach GmbH under the trade mark Sugi. Sugi is made from natural cotton and regenerated cellulose fibres and presented in various forms, for instance rectangular and triangular swabs. It is believed that the material is made via a process such as the process used in the early stages of cellulose regeneration.

The body can then be carboxymethylated by a method such as that described above or otherwise modified for instance by addition of other functional groups to the $C_6$, $C_2$ or $C_3$ carbon atoms of the cellulose ring via a reaction such as nucleophilic $SN_2$ substitution.

Following carboxymethylation the compressed body may have a reduced tendency for lateral wicking compared to that of the body prior to carboxymethylation. Reduction of lateral wicking in wound dressings is desirable because it can result in reduced maceration of the area surrounding the wound. This behaviour is not seen with foam dressings which tend to absorb over the whole area of the dressing.

Typically the carboxymethylated compressed body has lateral wicking values in the range of 45 to 55 mm when measured by the method described in the examples.

The invention is illustrated in the accompanying drawings in which:

FIG. 3 shows various properties for a compressed body similar to that in FIGS. 1 and 2, before and after chemical modification.

The invention will now be illustrated by the following examples.

Example 1

Figure 1:
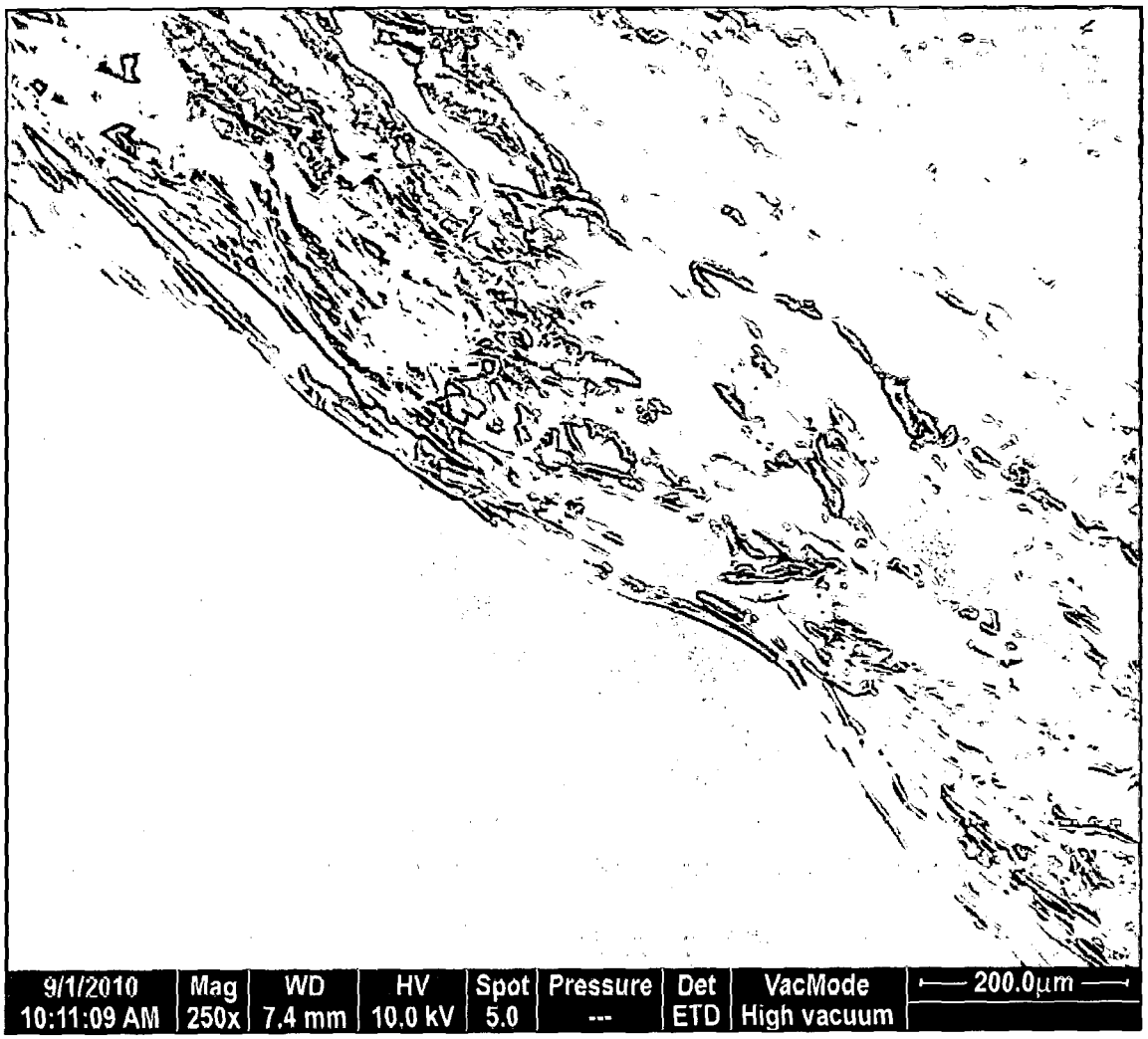
FIG. 1 shows a compressed body of cellulose (Sugi ex Kettenbach) prior to carboxymethylation.

FIG. 1 shows a compressed body of cellulose (Sugi swab) and having a basis weight of 594 $gm^{-2}$ at 250× magnification. The body is shown from the side, the Figure illustrating what appears to be an informal layer structure.

Figure 2:
FIG. 2 shows a compressed body of cellulose modified by carboxymethylation, after having been hydrated and air dried; the figure showing a cotton fibre surrounded by regenerated cellulose

FIG. 2 shows a compressed body of cellulose, modified by carboxymethylation. The figure shows the structure at 1000× magnification upon hydration and subsequent air drying.

Example 2

To establish the shrinkage and absorption properties of a carboxymethylated compressed body according to the invention, various tests were carried out on samples of Sugi material obtained from Kettenbach. The Sugi material is cellulose based but has not been chemically modified for instance by carboxymethylation. Various samples of Sugi were tested prior to and following carboxymethylation and the results compared. The modified body according to the invention was also compared to Aquacel, a carboxymethylated cellulose dressing made of non-woven mats of gel-forming fibers and available from ConvaTec. Aquacel typically has a density of 0.0773 $g/cm^{-3}$, substantially lower than that of a compressed structure.

The Sugi material was carboxymethylated using the following conditions. The cellulosic body was loaded into a reaction vessel. Reaction fluid is pumped through the cellulosic material at 70° C. for 90 minutes. The reaction fluid was a solution of an alkali (typically sodium hydroxide) (15.28 g in 68 g of water) and sodium monochloroacetate (22.96 g in 68 g of water) in 88 g methylated spirit. After the reaction time, the reaction was neutralised with acid (acetic acid 14 ml) for 10 minutes at 70° C. It was washed three times in a mixture of water and IMS for 10 minutes each time at 70° C. before being dried in a laboratory oven for 1 hour at 40° C.

The following properties of the unconverted and converted material were measured and compared: free swell absorbency and retention, tensile strength, lateral wicking and shrinkage.

Lateral wicking was measured by taking a dressing sample and cutting it to measure 10×1.5 cm in the machine and transverse direction. The dressing was placed in solution A dyed with Eosine and clamped in a vertical position for 1 minute. The sample was then removed and the distance moved by the dyed fluid measured.

Absorption was measured by taking a sample measuring 5 cm×5 cm and weighing it (W1). The sample was immersed in 40 times its weight of Solution A (physiological saline solution) for 30 minutes at 37° C. The sample was then held to drip for 30 seconds before being weighed (W2).

Absorption (g/g)=W2−W1/W1

Absorption (g/cm2)=W2−W1/area

Retention was measured by completing the absorption method and laying the sample onto a perforated metal grid. A weight equivalent to 40mmHg was applied to the sample for 1 minute. The weight was removed and the sample weighed (W3). Retention was calculated by:

Retention (g/g)=W3−W1/W1

Retention (g/cm2)=W3−W1/area

Tensile strength was measured by cutting a dressing sample to 10×2.5 cm in the machine and the transverse direction. The dressing was placed between jaws set 50 mm apart and using the Zwick Universal Tester was pulled apart and the tensile strength was calculated automatically. For wet tensile strength measurements, the sample was hydrated using Solution A for 1 minute before being tested.

Shrinkage was measured by cutting the sample to 5×5 cm and measuring in both directions using a steel ruler. The sample was then hydrated with excess solution A for a set period of time before being drained and measured again in both directions. The sample was allowed to dry out and was measured once more in both directions. The immediate and final area shrinkage can then be calculated.

Thickness was measured using a Hampden Soft Materials Thickness Gauge. When hydrated thickness is measured, the sample is hydrated with excess solution A before being measured.

Degree of Substitution was measured using acid-base titrations.

The samples tested were as follows:

| Reference | Sample | Degree of substitution |
| --- | --- | --- |
| HF-2010/198 | Sugi strip ex Kettenbach unmodified | 0.007 |
| HF-2010/229 | Sugi strip ex Kettenbach Modified | 0.234 |
| HF-2010/162 | Sugi A4 sheet ex Kettenbach Unmodified | 0.005 |
| HF-2010/230 | Sugi A4 sheet ex Kettenbach Modified | 0.089 |

The results are shown in FIG. 3. The results show that the chemically modified compressed material according to the invention does not shrink on contact with physiological saline solution in either lateral direction, the material increases in thickness by more than twice its original size on absorption of physiological saline solution. On drying out, the modified compressed material shrunk only slightly (up to 12.9% in the machine direction). Aquacel® shrunk in both lateral directions on initial contact with physiological saline solution up 22.0% (in the transverse direction). On contact with physiological saline solution Aquacel® increased in thickness by less than twice its original size.

The dry density of the chemically modified compressed material was found to be 0.1403 and 0.1889 gcm$^{-3}$ for the two samples of this material tested. The density of Aquacel® was an order of magnitude lower at 0.0773 gcm$^{-3}$ compared with that of the compressed material according to the invention.

On hydration with physiological saline solution the results show that the chemically modified compressed material of the invention swells in thickness by a greater ratio than Aquacel®. The compressed material had a ratio of 2.67 and 3.32 for the two samples tested, the Aquacel® swells by a ratio of 1.85.

Example 3

A wound model consisting of a thin layer of pork belly placed around the edge of a petridish was prepared to study the behaviour of the carboxymethylated cellulose sample from Example 1 on absorption of simulated exudate. Deliberate contours were made to the wound model in order to challenge the sample. A cross-section sample was laid against the wound model and Solution A dyed with Toluidine Blue O was added to the simulated wound bed slowly over a period of time. Microscopy images were captured every 5 seconds until full saturation of the dressing had occurred.

Results—On addition of the solution the dressing became gelled and expanded slightly to contour to the wound model. All of the deliberate contours which were made in the model became in direct contact with the dressing material. This example shows the advantage of the dressing material of the invention in establishing a close conformity with the wound on expansion of the dressing in the presence of fluid.

The invention claimed is:

1. A wound dressing comprising a compressed body of chemically modified cellulose, wherein the compressed body of chemically modified cellulose comprises a density in the range of 0.10 g.cm$^{-3}$ to 0.20 g.cm$^{-3}$, the compressed body of chemically modified cellulose having a thickness of from 3 mm to 4 mm, wherein the compressed body of chemically modified cellulose comprises a layered structure which is weakly associated, wherein lateral wicking of the dressing comprising the compressed body of chemically modified cellulose is from 10 to 55 mm, and wherein the dressing comprising the compressed body of chemically modified cellulose is capable of contacting a wound.

2. The dressing as claimed in claim 1 wherein the dressing expands on the absorption of wound fluid.

3. The dressing as claimed in claim 2 wherein the ratio of the thickness of the dressing pre hydration to the thickness of the dressing post hydration is greater than 2.

4. The dressing as claimed in claim 3, wherein the ratio of the thickness of the dressing pre-hydration to the thickness of the dressing post hydration is in the range of 2 to 3.5.

5. The dressing as claimed in claim 1 wherein the body has a lateral shrinkage on absorption of physiological saline of less than 5% when measured by the method described herein.

6. The dressing of claim 1, wherein the compressed body of chemically modified cellulose has lateral wicking values in the range of 45 to 55 mm.

7. The dressing of claim 1, wherein the compressed body of chemically modified cellulose has a thickness of from 3 mm to 3.5 mm.

8. The dressing of claim 1, wherein the compressed body of chemically modified cellulose has a free swell absorption in the range of 20 g/g to 25 g/g.

9. A wound dressing comprising a compressed body of cellulose, which has been chemically modified to increase its absorbency to at least 19 g/g as measured by the free swell method and which expands on absorption of wound fluid, wherein the compressed body of chemically modified cellulose has a density in the range of 0.10 g.cm$^{-3}$ to 0.20 g.cm$^{-3}$, wherein the compressed body of chemically modified cellulose comprises has a layered structure which is weakly associated, wherein the compressed body of chemically modified cellulose has a thickness of from 3 mm to 4 mm, wherein the dressing comprising the compressed body of chemically modified cellulose has a lateral wicking from 10 to 55 mm, and wherein the dressing comprising the compressed body of chemically modified cellulose is capable of contacting a wound.

10. The dressing as claimed in claim 9 wherein the ratio of the thickness of the dressing pre hydration to the thickness of the dressing post hydration is greater than 2.

11. The dressing as claimed in claim 9 wherein the body has a lateral shrinkage on absorption of physiological saline of less than 5% when measured by the method described herein.

12. The dressing as claimed in claim 9, wherein the ratio of the thickness of the dressing pre hydration to the thickness of the dressing post hydration is in the range of 2 to 3.5.

13. The dressing of claim 9, wherein the compressed body of chemically modified cellulose has lateral wicking values in the range of 45 to 55 mm.

14. The dressing of claim 9, wherein the compressed body of chemically modified cellulose has a free swell absorption in the range of 20 g/g to 25 g/g.

15. A process for making a wound dressing, the process comprising: obtaining a compressed body of cellulose having a density in the range of 0.10 to 0.20 g.cm$_{-3}$, wherein the compressed body of cellulose comprises associated layers which are weakly associated; and chemically modifying the compressed body of cellulose to increase its absorbency, wherein the chemically modified compressed body of cellulose has a thickness of at least about 3 mm, wherein lateral wicking of the dressing comprising the chemically modified compressed body of cellulose is from 45 to 55 mm, and wherein the dressing comprising the chemically modified compressed body of cellulose is capable of contacting a wound.

16. The process as claimed in claim 15 wherein the chemical modification is carboxymethylation.

17. The process as claimed in claim 15 wherein the compressed body of chemically modified cellulose expands on the absorption of wound fluid.

18. The process of claim 15, wherein the compressed body of chemically modified cellulose has a thickness of from 3 mm to 4 mm.

19. The process of claim 18, wherein the compressed body of chemically modified cellulose has a thickness of from 3 mm to 3.5 mm.

20. The process of claim 15, wherein the compressed body of chemically modified cellulose has a free swell absorption in the range of 20 g/g to 25 g/g.

* * * * *